United States Patent [19]

Kaltenbronn et al.

[11] 4,101,661

[45] Jul. 18, 1978

[54] NOVEL ANTIBACTERIAL AMIDE COMPOUNDS AND PROCESS MEANS FOR PRODUCING THE SAME

[75] Inventors: James S. Kaltenbronn; Theodore H. Haskell; Leonard Doub, all of Ann Arbor, Mich.

[73] Assignee: Warner-Lambert, Morris Plains, N.J.

[21] Appl. No.: 803,004

[22] Filed: Jun. 3, 1977

[51] Int. Cl.$^2$ .................. C07D 499/68; A61K 31/43; A61K 31/455

[52] U.S. Cl. ..................... 424/266; 424/246; 260/239.1; 544/21; 544/25; 544/27; 544/28; 544/24; 544/26; 544/30

[58] Field of Search .................. 260/239.1; 424/271, 424/266

[56] References Cited

U.S. PATENT DOCUMENTS

| | | | |
|---|---|---|---|
| 3,873,523 | 3/1975 | Doub et al. | 260/239.1 |
| 3,954,734 | 5/1976 | Doub et al. | 260/239.1 |

Primary Examiner—Gerald A. Schwartz

Attorney, Agent, or Firm—Stephen Raines; David B. Ehrlinger; Frank S. Chow

[57] ABSTRACT

Novel organic amide compounds which are N-[6-[(aminosulfonyl)phenyl]-1,2-dihydro-2-oxonicotinyl]-penicillin and cephalosporin type compounds having broad spectrum antibacterial utility are provided by (a) reacting the free amino acid of the appropriate penicillin or cephalosporin or the acid salt or silylated derivative or complex thereof with a reactive derivative of the corresponding N-6-[(aminosulfonyl)phenyl]-1,2-dihydro-2-oxonicotinic acid or (b) reacting the free amino acid 6-aminopenicillanic acid, 7-aminocephalosporanic acid, 7-amino-3-methylceph-3-em-4-carboxylic acid or a related compound or the acid salt or silylated derivative thereof with a reactive derivative of the corresponding D-N-[6-[(aminosulfonyl)phenyl]-1,2-dihydro-2-oxonicotinyl]-2-substituted glycine. Pharmaceutical compositions containing said compounds and methods for treating infections using said compositions are also disclosed.

13 Claims, No Drawings

NOVEL ANTIBACTERIAL AMIDE COMPOUNDS AND PROCESS MEANS FOR PRODUCING THE SAME

SUMMARY AND DETAILED DESCRIPTION

The present invention relates to novel chemical compounds that are useful as pharmacological agents and to methods for their production. More particularly, the invention relates to novel organic amide compounds having the formulae

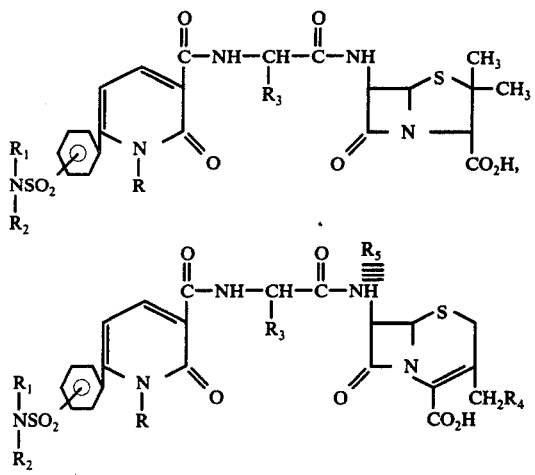

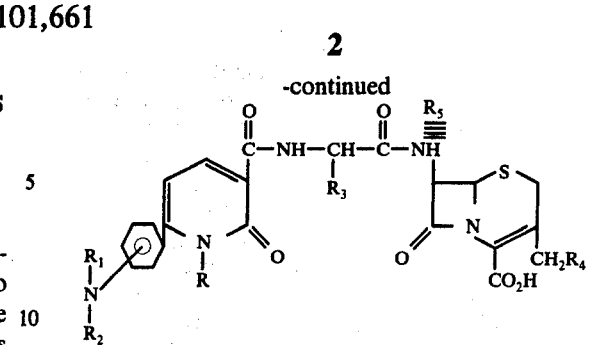

and pharmaceutically-acceptable salts thereof; wherein R is hydrogen or methyl; $R_1$ is hydrogen, lower alkyl or hydroxy(lower alkyl), $R_2$ is hydrogen, lower alkyl, hydroxy(lower alkyl), pyridyl or di(lower alkyl)amino(lower alkyl); $R_1R_2N$ taken together is 1-pyrrolidinyl, 1-piperidinyl or hydroxymethyl-1-piperidinyl, $R_3$ is phenyl, 4-hydroxyphenyl, 2-thienyl or cyclohexa-1,4-dien-1-yl; $R_4$ is hydrogen, acetoxy, a heterocyclicthio group where the heterocyclic moiety is an optionally methyl substituted thiadiazolyl, triazolyl or tetrazolyl group or 1-pyridyl and $R_5$ is hydrogen or methoxy, with the proviso that when $R_4$ is 1-pyridyl, the $CO_2H$ is $CO_2^-$.

The preferred compounds are those wherein R is hydrogen; $R_1$ and $R_2$ are hydroxy(lower alkyl). The most preferred compounds are those wherein R is hydrogen, $R_1$ and $R_2$ are hydroxyethyl, $R_3$ is p-hydroxyphenyl and the $R_1R_2NSO_2$ group is in the para position. The term "lower alkyl" is intended to represent a hydrocarbon moiety of from one to six carbon atoms, such as methyl, ethyl, cyclopropyl, etc.

In accordance with the invention the foregoing amide compounds having the formulae

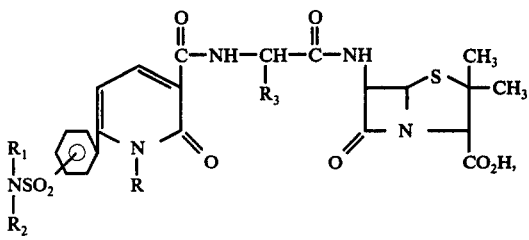

and pharmaceutically acceptable salts thereof wherein R, $R_1$, $R_2$, $R_1R_2N$, $R_3$, $R_4$ and $R_5$ are as previously defined are produced by reacting a compound of the formulae

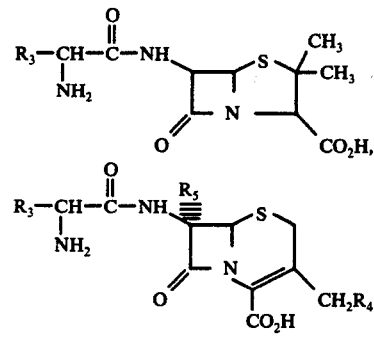

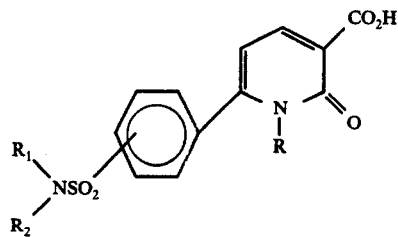

or the acid salt, silylated derivative (preferably the disilylated) or complex (preferably the dimethylsulfoxide) thereof wherein $R_3$ and $R_4$ are as previously defined, with a reactive derivative of a 1,2-dihydro-2-oxonicotinic acid compound having the formula or its acid addition salt, where R, $R_1$ and $R_2$ all have the aforementioned significance.

Some examples of reactive derivatives of the 6-[(aminosulfonyl)phenyl]-1,2-dihydro-2-oxonicotinic acid compound suitable for the reaction are the acid halides (especially the acid chloride), the imidazolide, mixed anhydrides (especially those formed from an alkyl chloroformate such as ethyl chloroformate and isobutyl chloroformate), and activated esters such as the pentachlorophenyl ester and N-hydroxysuccinimide ester.

The reactants are normally employed in approximate equimolar quantities, although an excess of either (oxonicotinic acid compound or amino acid compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the penicillin and cephalosporin type compounds in the free acid or salt form, aqueous solutions may be used for acylation with an acid halide or mixed anhydride under normal Schotten-Baumann conditions. The duration and temperature of the reaction are not critical. Temperatures in the range from −30° to +30° C. are commonly used for reaction times ranging from a few hours up to a day or more. The product may be isolated in any suitable way as the free acid or as a salt by appropriate adjustment of the pH.

The reactive derivative of 6-[(aminosulfonyl)phenyl]-1,2-dihydro-2-oxonicotinic acid compounds and acid-addition salts which are required as starting materials in the foregoing process can be prepared according to any of a variety of methods.

A 6-[(aminosulfonyl)phenyl]-1,2-dihydro-2-oxonicotinic acid may be converted to its acid chloride utilizing thionyl chloride, its mixed anhydride utilizing ethyl chloroformate, its pentachlorophenyl ester by esterification with pentachlorophenol and its imidazolide by reacting the acid with 1,1'-carbonyldiimidazole.

The silylated amino acid starting materials can be prepared by reacting an amino acid of the formulae

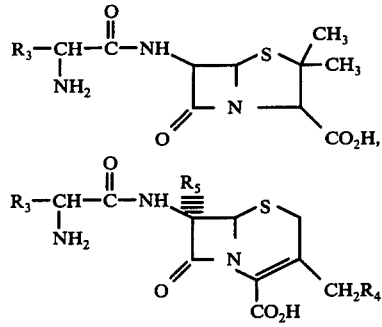

or a salt thereof wherein $R_3$, $R_4$ and $R_5$ are as previously defined in anhydrous form with either one or two equivalents of a tri(lower alkyl)silyl chloride in the presence of triethylamine. The preferred silylating agents are trimethylsilyl chloride and dimethyl dichlorosilane. When two equivalents of the silylating agent are used, both the amino and the carboxyl group become silylated. When one equivalent is used, only the carboxyl group is silylated. Both the mono- and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formulae

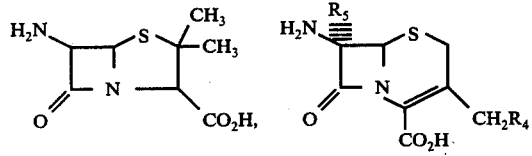

or the corresponding acid salt or silylated derivative thereof with a reactive derivative of D-N-[6-[(aminosulfonyl)phenyl]-1,2-dihydro-2-oxonicotinyl]-2-substituted glycine having the formula

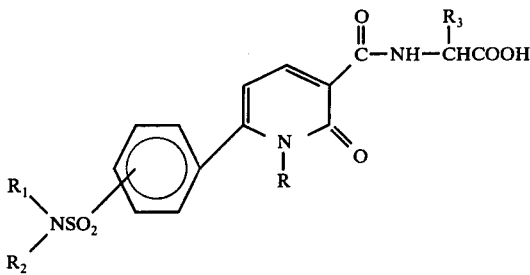

or its acid addition salts where R, $R_1$, $R_2$, $R_3$, $R_4$ and $R_5$ have the aforementioned significance.

Some examples of reactive derivatives of the D-N-(1,2-dihydro-2-oxonicotinyl)-2-substituted glycine compounds suitable for the reaction are the acid halides, the imidazolide, mixed anhydrides (especially those formed from an alkyl chloroformate such as ethyl chloroformate and isobutyl chloroformate), and activated esters such as the pentachlorophenyl ester and N-hydroxysuccinimide ester. Since racemization is more likely with the acid halide, the other forms are generally preferred. The reactants are normally employed in approximate equimolar quantities, although an excess of either (oxonicotinic acid compound or amino acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, 6-aminopenicillanic acid and 7-amino-3-$R_4CH_2$ceph-3-em-4 carboxylic acid may be reacted with an acid chloride or mixed anhydride in the free acid or salt form using aqueous solutions under normal Schotten-Baumann conditions. The duration and temperature of the reaction are not critical. Temperatures in the range from −30° to +30° C. are commonly used for reaction times ranging from a few hours up to a day or more. The product may be isolated in any suitable way as the free acid or as a salt by appropriate adjustment of the pH.

The reactive derivative of N-[6-[(aminosulfonyl)phenyl]-1,2-dihydro-2-oxonicotinyl]-2-substituted glycines or their acid-addition salts which are required as starting materials in the foregoing process can be prepared by methods illustrated in greater detail hereinafter.

N-[6-[(aminosulfonyl)phenyl]-1,2-dihydro-2-oxonicotinyl]-2-substituted glycine compounds may be prepared by reacting the corresponding reactive derivative of 6-[(aminosulfonyl)phenyl]-1,2-dihydro-2-oxonicotinic acid, such as acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formulae

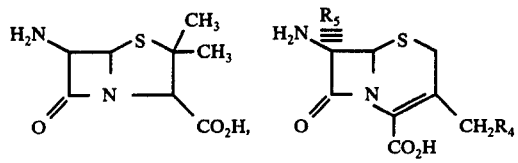

with a hexaalkyldisilazane. The preferred silylating agent is hexamethyldisilazane. Only the carboxyl group is silylated under the conditions used (e.g., 2-hour reflux in dichloromethane). After acylation, the silyl group is easily removed by treatment with water.

The free acids of the invention form carboxylate salts with any of a variety of inorganic and organic bases. Pharmaceutically-acceptable carboxylate salts are formed by reacting the free acids with such bases as sodium hydroxide, sodium carbonate, sodium bicarbonate, sodium 2-ethylhexanoate, potassium hydroxide, potassium carbonate, potassium 2-ethylhexanoate, calcium hydroxide, ethylamine, 2-hydroxyethylamine, and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention. In addition, certain of the compounds of the invention can exist in the form of an acid-addition salt, namely where $R_2$ is pyridyl or di(-lower alkyl)amino(lower alkyl). Pharmaceutically-acceptable salts are formed by reaction of the free base of a carboxylate salt with any of a number of inorganic and organic acids, including hydrochloric, sulfuric, nitric, phosphoric, acetic, benzoic, citric, maleic, malic, tartaric, succinic, gluconic, ascorbic, sulfamic, pamoic, methanesulfonic, benzenesulfonic, and related acids.

The compounds of the invention can exist in anhydrous form, as well as in solvated, including hydrated, forms. In general, the hydrated forms and the solvated forms with pharmaceutically-acceptable solvents are equivalent to the anhydrous or unsolvated forms for the purposes of the invention.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table for certain of the preferred compounds. The compounds shown in the table are those wherein R is hydrogen and are in the form of their sodium salt.

Thus, the compounds of this invention and their non-toxic pharmaceutically-acceptable salts are highly useful as broad spectrum antibiotics in mammals when administered in amounts ranging from about 5 mg. to about 100 mg. per kg. of body weight per day. A preferred dosage regimen for optimum results would be from about 10 mg. to about 50 mg. per kg. of body weight per day, and such dosage units are employed that a total of about 700 mg. to about 3500 mg. of active ingredient for a subject of about 70 kg. body weight are administered in a 24 hour period in an appropriate pharmaceutical composition.

While the compounds of this invention may be administered orally in the form of tablets, capsules, syrups, etc., the preferred route of administration is parenterally for treating systemic infections.

ACTIVITY TABLE

| | | | | | | | Minimal Inhibitory Concentration, μg/ml., vs.: | | | |
|---|---|---|---|---|---|---|---|---|---|---|
| $R_1$ | $R_2$ | $R_3$ | $R_4$ | $R_5$ | Position (a) | Nucleus (b) | Klebsiella pneumoniae MGH-1 or-2 (c) | Serratia marcescens IMM-5 | Enterobacter cloacae IMM-11 or-50 | Pseudomonas aeruginosa 28 or CB-CS |
| $HOCH_2CH_2$ | $HOCH_2CH_2$ | p-(HO)-$C_6H_4$ | — | — | p | P | 25 (2) | 100 | 12.5 | 6.3 (28) |
| H | H | $C_6H_5$ | — | — | m | P | 0.8 (1) | 50 | 1.6 (50) | 3.1 |
| $CH_3$ | H | $C_6H_5$ | — | — | p | P | 3.1 | 50 | 3.1 | 3.1 (28) |
| H | H | $C_6H_5$ | — | — | p | P | 3.1 (2) | 100 | 6.3 | 6.3 |
| $CH_3$ | $CH_3$ | $C_6H_5$ | — | — | p | P | 0.8 (1) | 25 | 1.6 (11) | 1.6 |
| 3-pyridyl | H | $C_6H_5$ | — | — | p | P | 6.3 (1) | 100 | 6.3 (11) | 6.3 |
| 2-pyridyl | H | $C_6H_5$ | — | — | p | P | 3.1 (1) | 100 | 3.1 (11) | 3.1 (CB-CS) |
| $-CH_2-CH_2-CH_2-CH_2-$ | | $C_6H_5$ | — | — | p | P | 0.8 (2) | 25 | 3.1 | 6.3 |
| $-CH_2CH_2CH_2CH_2CH_2-$ | | $C_6H_5$ | — | — | p | P | 1.6 (1) | 25 | 3.1 (11) | 3.1 (28) |
| $C_2H_5$ | $C_2H_5$ | $C_6H_5$ | — | — | p | P | 1.6 (1) | 12.5 | 1.6 (11) | 0.8 (CB-CS) |
| $HOCH_2CH_2$ | $HOCH_2CH_2$ | $C_6H_5$ | — | — | p | P | 1.6 (1) | 100 | 3.1 (11) | 3.1 |
| $CH_3$ | $CH_3$ | p-(HO)-$C_6H_4$ | — | — | p | P | 6.3 (2) | 100 | 6.3 | 1.6 (28) |
| $HOCH_2CH_2$ | H | $C_6H_5$ | — | — | p | P | 6.3 (2) | 100 | 6.3 | 6.3 (28) |
| $-CH_2CHCH_2CH_2CH_2-$ with $CH_2OH$ | | $C_6H_5$ | — | — | p | P | 6.3 (2) | 50 | 3.1 (11) | 12.5 (28) |
| $(CH_3)_2N(CH_2)_2$ | H | $C_6H_5$ | — | — | p | P | 12.5 (2) | 200 | 6.3 | 6.3 (28) |
| $(CH_3)_2N(CH_2)_2$ | H | p-(HO)-$C_6H_5$ | — | — | p | P | 3.1 (2) | — | 1.6 (11) | 0.8 (28) |
| $CH_3$ | H | $C_6H_5$ | $CH_3CO_2$ | H | p | C | 6.3 (1) | 200 | 6.3 (11) | 25 (28) |
| $HOCH_2CH_2$ | $HOCH_2$ | $C_6H_5$ | $CH_3CO_2$ | H | p | C | 1.6 (2) | 200 | 6.3 (11) | 12.5 |

ACTIVITY TABLE-continued

| R₁ | R₂ | R₃ | R₄ | R₅ | Position (a) | Nucleus (b) | Klebsiella pneumoniae MGH-1 or-2 (c) | Serratia marcescens IMM-5 | Enterobacter cloacae IMM-11 or-50 | Pseudomonas aeruginosa 28 or CB-CS |
|---|---|---|---|---|---|---|---|---|---|---|
| CH₃ | CH₂CH₃ | C₆H₅ | CH₃CO₂ | —CH₃O | p | C | 6.3 (2) | 200 | 12.5 (11) | — |
| CH₃ | CH₂CH₃ | C₆H₅ | N——N (CH₃-S-S ring) | H | p | C | 0.4 (2) | 25 | 0.8 (11) | 6.3 (28) |
| CH₃ | CH₃ | C₆H₅ | CH₃CO₂ | H | p | C | 3.1 | 200 | 6.3 | 6.3 (CB-CS) |
| HOCH₂CH₂ | HOCH₂CH₂ | C₆H₅ | N——N (CH₃-S-S ring) | H | p | C | 0.8 | — | 3.1 | 12.5 |

(a) Shows the position of the R₁R₂NSO₂ group on the phenyl ring.
(b) Nucleus indicates if the group are on a penicillin (P) or a cephalosporin (C) nucleus.
(c) Where strain is not designated, the M.I.C. value applies to both.

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 50 mg. to about 1000 mg. of active compound per vial. The vial may also contain other active ingredients, buffers, salts, etc. The sterile material in the vial is dissolved in water for injection at the time of use. Oral preparations would also have from about 50 mg. to about 1000 mg. of active compound per unit dose form.

The invention is illustrated by the following examples.

EXAMPLE 1

6-[4-[bis(2-hydroxyethyl)aminosulfonyl]phenyl]-1,2-dihydro-2-oxonicotinic acid, 2,5-dioxo-1-pyrrolidinyl ester, 20 g. is added to a stirred mixture of 25.5 g. of an amoxicillindimethyl sulfoxide complex and 400 ml. of dimethyl sulfoxide, cooled in an ice bath. The mixture is stirred at room temperature for 4 hours and the resulting solution is poured into 500 ml. of ice water and acidified to pH 2.0 with dilute hydrochloric acid. The resulting precipitate of N-[6-[4-[bis(2-hydroxyethyl)aminosulfonyl]phenyl]-1,2-dihydro-2-oxonicotinyl]amoxicillin is collected by filtration and washed thoroughly with cold water. The solid is suspended in 400 ml. of cold water and the pH is brought to 6.0 with 1N aqueous sodium hydroxide. The resulting solution is clarified by filtration and freeze-dried to give N-[6-[4-[bis(2-hydroxyethyl)aminosulfonyl]phenyl]-1,2-dihydro-2-oxonicotinyl]amoxicillin, sodium salt; $[\alpha]_D^{23} = +146°$ (1.0% in methanol); iodometric assay, 95.6%.

EXAMPLE 2

A stirred suspension of 3.97 g. of the triethylamine salt of ampicillin (U.S. Pat. No. 3,954,734) in 60 ml. of N,N-dimethylacetamide is cooled to 0°–5° C. and treated in turn with 2.23 ml. of trimethylsilyl chloride and 1.24 ml. of triethylamine. The mixture is stirred at room temperature for 1 hour, then cooled to 0°–5° and treated in turn with 1.24 ml. of triethylamine and 2.76 g. of 6-[3-(aminosulfonyl)phenyl]-1,2-dihydro-2-oxonicotinyl chloride. The mixture is stirred at 0°–5° C. for 30 minutes, then at room temperature for 16 hours. The mixture is poured into 200 ml. of ice water and the pH is adjusted to 2.0 with dilute hydrochloric acid. The resulting precipitate of N-[6-[3-(aminosulfonyl)phenyl]-1,2-dihydro-2-oxonicotinyl]ampicillin is collected by filtration, washed with water and dried. The solid is suspended in 75 ml. of cold water and the pH is brought to 8.0 with 2N aqueous sodium hydroxide. The resulting solution is clarified by filtration and freeze-dried to give N-[6-[3-(aminosulfonyl)phenyl]-1,2-dihydro-2-oxonicotinyl]ampicillin, sodium salt; $[\alpha]_D^{23} = +131°$ (0.99% in methanol); iodometric assay, 80.9%.

EXAMPLE 3

A stirred suspension of 7.28 g. of the triethylamine salt of ampicillin in 120 ml. of N,N-dimethylacetamide is cooled to 0°–5° C. and treated in turn with 4.1 ml. of trimethylsilyl chloride and 2.26 ml. of triethylamine. The mixture is stirred at room temperature for 1 hour, then cooled to 0°–5° C. and treated in turn with 5.29 g. of 6-[4-(methylaminosulfonyl)phenyl]-1,2-dihydro-2-oxonicotinyl chloride and 2.26 ml. of triethylamine. The mixture is stirred at 0°–5° C. for 30 minutes, then at room temperature for 16 hours. The mixture is poured into 400 ml. of ice water and the pH is adjusted to 2.1 with dilute hydrochloric acid. The resulting precipitate of N-[6-[4-(methylaminosulfonyl)phenyl]-1,2-dihydro-2-oxonicotinyl]ampicillin is collected by filtration, washed with water and dried. The solid is dissolved in 75 ml. of tetrahydrofuran and 8.5 ml. of 50% sodium 2-ethylhexanoate in n-butanol is added to the solution. The resulting mixture is diluted with 150 ml. of ether and the precipitated N-[6-[4-(methylaminosulfonyl)phenyl]-1,2-dihydro-2-oxonicotinyl]ampicillin, sodium salt removed by filtration, washed with ether and dried; $[\alpha]_D^{23} = +141°$ (1.02% in methanol); iodometric assay, 81.8%.

EXAMPLE 4

A stirred suspension of 5.89 g. of the triethylamine salt of ampicillin in 100 ml. of N,N-dimethylacetamide is cooled to 0°–5° C. and treated in turn with 3.31 ml. of trimethylsilyl chloride and 1.83 ml. of triethylamine. The mixture is stirred at room temperature for 1 hour, then cooled to 0°–5° C. and treated in turn with 1.83 ml.

of triethylamine and 4.1 g. of 6-[4-(aminosulfonyl)-phenyl]-1,2-dihydro-2-oxonicotinyl chloride. The mixture is stirred at 0°–5° C. for 30 minutes, then at room temperature for 16 hours. The mixture is poured into 300 ml. of ice water and the pH is adjusted to 2.1 with dilute hydrochloric acid. The resulting precipitate of N-[6-[4-(aminosulfonyl)phenyl]-1,2-dihydro-2-oxonicotinyl]ampicillin is collected by filtration, washed with water and dried. The solid is dissolved in 50 ml. of tetrahydrofuran and 5.0 ml. of 50% sodium 2-ethylhexanoate in n-butanol is added to the solution. The resulting mixture is diluted with 150 ml. of ether and the precipitated N-[6-[4-(aminosulfonyl)phenyl]-1,2-dihydro-2-oxonicotinyl]ampicillin, sodium salt removed by filtration, washed with ether and dried; $[\alpha]_D^{23} = +142°$ (1.03% in methanol); iodometric assay, 73.9%.

EXAMPLE 5

A stirred suspension of 4.9 g. of the triethylamine salt of ampicillin in 100 ml. of N,N-dimethylacetamide is cooled to 0°–5° C. and treated in turn with 2.75 1 ml. of trimethylsilyl chloride and 1.55 ml. of triethylamine. The mixture is stirred at room temperature for 1 hour, then cooled to 0°–5° C. and treated in turn with 1.55 ml. of triethylamine and 3.71 g. of 6-[4-(dimethylaminosulfonyl)phenyl]-1,2-dihydro-2-oxonicotinyl chloride. The mixture is stirred at 0°–5° C. for 30 minutes, then at room temperature for 16 hours. The mixture is poured into 300 ml. of ice water and the pH is adjusted to 2.0 with dilute hydrochloric acid. The resulting precipitate of N-[6-[4-(dimethylaminosulfonyl)phenyl]-1,2-dihydro-2-oxonicotinyl]ampicillin is collected by filtration, washed with water and dried. The solid is dissolved in 75 ml. of N,N-dimethylacetamide and 3.8 ml. of 50% sodium 2-ethylhexanoate in n-butanol is added to the solution. The resulting solution is poured into 250 ml. of ethyl acetate. The precipitated N-[6-[4-(dimethylaminosulfonyl)phenyl]-1,2-dihydro-2-oxonicotinyl]ampicillin, sodium salt is collected by filtration, washed with ethyl acetate and dried; $[\alpha]_D^{23} = +152°$ (1.0% in methanol); iodometric assay, 90.2%.

EXAMPLE 6

A stirred suspension of 4.85 g. of the triethylamine salt of ampicillin in 100 ml. of N,N-dimethylacetamide is cooled to 0°–5° C. and treated in turn with 1.5 ml. of triethylamine and 2.75 ml. of trimethylsilyl chloride. The mixture is stirred at room temperature for 1 hour, then cooled to 0°–5° C. and treated in turn with 3.0 ml. of triethylamine and 4.6 g. of 6-[4-(3-pyridylaminosulfonyl)phenyl]-1,2-dihydro-2-oxonicotinyl chloride hydrochloride. The mixture is stirred at 0°–5° C. for thirty minutes, then at room temperature for 16 hours. The mixture is poured into 300 ml. of ice water and the pH is adjusted to 3.0 with dilute hydrochloric acid. The resulting precipitate of N-[6-[4-(3-pyridylaminosulfonyl)phenyl]-1,2-dihydro-2-oxonicotinyl]ampicillin is collected by filtration, washed with water and dried. The solid is dissolved in 100 ml. of N,N-dimethylacetamide and 2.5 ml. of 50% sodium 2-ethylhexanoate in n-butanol is added to the solution. The resulting solution is poured into 300 ml. of ethyl acetate. The precipitated N-[6-[4-(3-pyridylaminosulfonyl)phenyl]-1,2-dihydro-2-oxonicotinyl]ampicillin, sodium salt is collected, washed with ethyl acetate and dried; $[\alpha]_D^{23} = +110°$ (1.04% in methanol); iodometric assay, 67%.

EXAMPLE 7

By substituting 4.6 g. of 6-[4-(2-pyridylaminosulfonyl)phenyl]-1,2-dihydro-2-oxonicotinyl chloride hydrochloride for the 6-[4-(3-pyridylaminosulfonyl)phenyl]-1,2-dihydro-2-oxonicotinyl chloride hydrochloride in Example 6, there is obtained the sodium salt of N-[6-[4-(2-pyridylaminosulfonyl)phenyl]-1,2-dihydro-2-oxonicotinyl]ampicillin; $[\alpha]_D^{23} = +174°$ (1.02% in methanol); iodometric assay 75.7%.

EXAMPLE 8

A stirred suspension of 5.17 g. of the triethylamine salt of ampicillin in 100 ml. of N,N-dimethylacetamide is cooled to 0°–5° C. and treated in turn with 2.91 ml. of trimethylsilyl chloride and 1.61 ml. of triethylamine. The mixture is stirred at room temperature for 1 hour, then cooled to 0°–5° C. and treated in turn with 1.61 ml. of triethylamine and 4.22 g. of 6-[4-(1-pyrrolidinylsulfonyl)phenyl]-1,2-dihydro-2-oxonicotinyl chloride. The mixture is stirred at 0°–5° C. for thirty minutes, then at room temperature for 16 hours. The mixture is poured into 300 ml. of ice water and the pH is adjusted to 2.5 with dilute hydrochloric acid. The resulting precipitate of N-[6-[4-(1-pyrrolidinylsulfonyl)phenyl]-1,2-dihydro-2-oxonicotinyl]ampicillin is collected by filtration, washed well with water and dried. The solid is dissolved in 100 ml. of N,N-dimethylacetamide and 3.7 ml. of 50% sodium 2-ethylhexanoate in n-butanol is added to the solution. The resulting solution is poured into 300 ml. of ethyl acetate. The N-[6-[4-(1-pyrrolidinylsulfonyl)phenyl]-1,2-dihydro-2-oxonicotinyl]ampicillin, sodium salt is collected, washed with ethyl acetate and dried; $[\alpha]_D^{23} = +147°$ (1.02% in methanol); iodometric assay, 90.2%.

EXAMPLE 9

A stirred suspension of 6.2 g. of the triethylamine salt of ampicillin in 150 ml. of N,N-dimethylacetamide is cooled to 0°–5° C. and treated in turn with 3.5 ml. of trimethylsilyl chloride and 2.0 ml. of triethylamine. The mixture is stirred at room temperature for 1 hour, then cooled to 0°–5° C. and treated in turn with 2.0 ml. of triethylamine and 5.26 g. of 6-[4-(1-piperidinylsulfonyl)phenyl]-1,2-dihydro-2-oxonicotinyl chloride. The mixture is stirred at 0°–5° C. for 30 minutes, then at room temperature for 16 hours. The mixture is poured into 400 ml. of ice water and the pH is adjusted to 2.0 with dilute hydrochloric acid. The resulting precipitate of N-[6-[4-(1-piperidinylsulfonyl)phenyl]-1,2-dihydro-2-oxonicotinyl]ampicillin is collected by filtration, washed well with water and dried. The solid is dissolved in 100 ml. of methylene chloride and 4.5 ml. of 50% sodium 2-ethylhexanoate in n-butanol is added to the solution. The resulting solution is diluted with 400 ml. of ethyl acetate. The precipitated N-[6-[4-(1-piperidinylsulfonyl)phenyl]-1,2-dihydro-2-oxonicotinyl]ampicillin, sodium salt is collected by filtration, washed with ethyl acetate and dried; $[\alpha]_D^{23} = +124°$ (1.02% in methanol); iodometric assay, 82.8%.

EXAMPLE 10

A stirred suspension of 7.7 g. of the triethylamine salt of ampicillin in 200 ml. of N,N-dimethylacetamide is cooled to 0°–5° C. and treated in turn with 4.35 ml. of trimethylsilyl chloride and 2.4 ml. of triethylamine. The mixture is stirred at room temperature for 1 hour, then cooled to 0°–5° C. and treated in turn with 2.4 ml. of triethylamine and 6.3 g. of 6-[4-(diethylaminosulfonyl)-phenyl]-1,2-dihydro-2-oxonicotinyl chloride. The mixture is stirred at 0°–5° C. for 30 minutes, then at room temperature for 16 hours. The mixture is poured into 500 ml. of ice water and the pH is adjusted to 2.0 with dilute hydrochloric acid. The resulting precipitate of N-[6-[4-diethylaminosulfonyl)phenyl]-1,2-dihydro-2-oxonicotinyl]ampicillin is collected by filtration, washed well with water and dried. The solid is dissolved in 100 ml. of N,N-dimethylacetamide and 5.0 ml. of 50% sodium 2-ethylhexanoate in n-butanol is added to the solution. The resulting solution is poured into 400 ml. of ethyl acetate. The precipitated N-[6-[4-(diethylaminosulfonyl)phenyl]-1,2-dihydro-2-oxonicotinyl]ampicillin, sodium salt is collected, washed with ethyl acetate and dried; $[\alpha]_D^{23} = +150°$ (1.0% in methanol; iodometric assay, 92.2%.

EXAMPLE 11

A stirred suspension of 28.1 g. of the triethylamine salt of ampicillin in 500 ml. of N,N-dimethylacetamide is cooled to 0°–5° C. and treated in turn with 15.8 ml. of trimethylsilyl chloride and 8.72 ml. of triethylamine. The mixture is stirred at room temperature for 1 hour, then cooled to 0°–5° C. and treated with 30.0 g. of 6-[4-[bis-(2-hydroxyethyl)aminosulfonyl]phenyl]-1,2-dihydro-2-oxonicotinic acid, 2,5-dioxo-1-pyrrolidinyl ester. The mixture is stirred at 0°–5° C. for 30 minutes, then at room temperature for 16 hours. The mixture is poured into 1 l. of ice water and the ph is adjusted to 2.0 with dilute hydrochloric acid. The resulting precipitate of N-[6-[4-[bis-(2-hydroxyethyl)aminosulfonyl]phenyl]-1,2-dihydro-2-oxonicotinyl]ampicillin is collected by filtration and washed well with cold water. The solid is suspended in 400 ml. of cold water and the pH is brought to 7.5 with 1N aqueous sodium hydroxide. The resulting solution is clarified by filtration and freeze-dried to give N-[6-[4-[bis(2-hydroxyethyl)aminosulfonyl]phenyl]-1,2-dihydro-2-oxonicotinyl]ampicillin, sodium salt; $[\alpha]_D^{23} = +148°$ (1.0% in methanol); iodometric assay, 94.9%.

EXAMPLE 12

A stirred solution of 13.2 g. of an amoxicillin-dimethyl sulfoxide complex in 200 ml. of N,N-dimethylacetamide is cooled to 0°–5° C. and treated in turn with 7.5 g. of 6-[4-(dimethylaminosulfonyl)phenyl]-1,2-dihydro-2-oxonicotinyl imidazolide and 2.7 ml. of triethylamine. The solution is stirred at room temperature for 6 hours, then clarified by filtration and poured into 500 ml. of ice water acidified with 20 ml. of 1N hydrochloric acid. The pH of the mixture is adjusted to 3.0 with dilute hydrochloric acid and the resulting precipitate of N-[6-[4-(dimethylaminosulfonyl)phenyl]-1,2-dihydro-2-oxonicotinyl]amoxicillin is collected by filtration and washed well with water. The solid is suspended in 350 ml. of cold water and the pH is brought to 6.7 with 1N aqueous sodium hydroxide. The resulting solution is clarified by filtration and freeze-dried to give N-[6-[4-(dimethylaminosulfonyl)phenyl]-1,2-dihydro-2-oxonicotinyl]amoxicillin, sodium salt; $[\alpha]_D^{23} = +180°$ (1.0% in 75% dimethylformamide/pyridine); iodometric assay, 86%.

EXAMPLE 13

A stirred suspension of 3.73 g. of the triethylamine salt of ampicillin in 50 ml. of N,N-dimethylacetamide is cooled to 0°–5° C. and treated in turn with 2.1 ml. of trimethylsilyl chloride and 1.16 ml. of triethylamine. The mixture is stirred at room temperature for 1 hour, then cooled to 0°–5° C. and treated with 3.61 g. of 6-[4-[(2-hydroxyethyl)aminosulfonyl]phenyl]-1,2-dihydro-2-oxonicotinic acid, 2,5-dioxo-1-pyrrolidinyl ester. The mixture is stirred at 0°–5° C. for 30 minutes, then at room temperature for 16 hours. The mixture is poured into 200 ml. of ice water and the pH is adjusted to 2.0 with dilute hydrochloric acid. The resulting precipitate of N-[6-[4-[(2-hydroxyethyl)aminosulfonyl]phenyl]-1,2-dihydro-2-oxonicotinyl]ampicillin is collected by filtration and washed well with water. The solid is suspended in 75 ml. of cold water and the pH is brought to 7.5 with 1N aqueous sodium hydroxide. The resulting solution is clarified by filtration and freeze-dried to give the sodium salt. This sodium salt is dissolved in 50 ml. of cold methanol. The solution is diluted with sufficient 2-propanol to precipitate the sodium salt, which is collected by filtration and then dissolved in 80 ml. of cold water. The aqueous solution is freeze-dried to give the purified N-[6-[4-[(2-hydroxyethyl)aminosulfonyl]phenyl]-1,2-dihydro-2-oxonicotinyl]ampicillin, sodium salt; $[\alpha]_D^{23} = +157°$ (1.03% in methanol); iodometric assay, 95.1%.

EXAMPLE 14

A stirred suspension of 3.4 g. of the triethylamine salt of ampicillin in 50 ml. of N,N-dimethylacetamide is cooled to 0°–5° C. and treated in turn with 1.91 ml. of trimethylsilyl chloride and 1.05 ml. of triethylamine. The mixture is stirred at room temperature for 1 hour, then cooled to 0°–5° C. and treated with 3.7 g. of 6-[4-[(3-hydroxymethyl-1-piperidinyl)sulfonyl]phenyl]-1,2-dihydro-2-oxonicotinic acid, 2,5-dioxo-1-pyrrolidinyl ester. The mixture is stirred at 0°–5° C. for 30 minutes, then at room temperature for 16 hours. The mixture is poured into 200 ml. of ice water and the pH is adjusted to 2.0 with dilute hydrochloric acid. The resulting precipitate of N-[6-[4-[(3-hydroxymethyl-1-piperidinyl)sulfonyl]phenyl]-1,2-dihydro-2-oxonicotinyl]ampicillin is collected by filtration and washed well with water. The solid is suspended in 75 ml. of cold water and the pH is brought to 7.5 with 1N aqueous sodium hydroxide. The resulting solution is clarified by filtration and freeze-dried to give N-[6-[4-[(3-hydroxymethyl-1-piperidinyl)sulfonyl]phenyl]-1,2-dihydro-2-oxonicotinyl]ampicillin, sodium salt; $[\alpha]_D^{23} = +140°$ (1.01% in methanol); iodometric assay, 93.2%.

EXAMPLE 15

A stirred suspension of 4.31 g. of the triethylamine salt of ampicillin in 60 ml. of N,N-dimethylacetamide is cooled to 0°–5° C. and treated in turn with 2.67 ml. of triethylamine and 4.03 g. of 6-[4-[(2-dimethylaminoethyl)aminosulfonyl]phenyl]-1,2-dihydro-2-oxonicotinyl chloride hydrochloride. The mixture is stirred at 0°–5° C. for 30 minutes, then at room temperature for 16 hours. The mixture is filtered and the filtrate is poured into a mixture of 150 ml. of ethyl acetate and 150 ml. of ether. The precipitated solid is collected by filtration, washed with ether and dried. The solid is suspended in 75 ml. of cold water and the pH is brought to 7.8 with 1N aqueous sodium hydroxide. The resulting solution is clarified by filtration and freeze-dried to give N-[6-[4-[(dimethylaminoethyl)aminosulfonyl]phenyl]1,2-dihydro-2-oxonicotinyl]ampicillin, sodium salt; $[\alpha]_D^{23} = +121°$ (1.02% in 50% methanol/pH7 phosphate buffer); iodometric assay, 69.9%.

EXAMPLE 16

A stirred solution of 5.73 g. of an amoxicillin-dimethyl sulfoxide complex in 80 ml. of N,N-dimethylacetamide is cooled to 0°–5° C. and treated in turn with 3.97 ml. of triethylamine and 4.0 g. of 6-[4-[(2-dimethylaminoethyl)aminosulfonyl]phenyl]-1,2-dihydro-2-oxonicotinyl chloride hydrochloride. The mixture is stirred at 0°–5° C. for 30 minutes, then at room temperature for 16 hours. The mixture is filtered to remove triethylamine hydrochloride and the filtrate is poured into 300 ml. of ethyl acetate. The precipitated solid is collected by filtration, washed with ethyl acetate and dried. The solid is suspended in 75 ml. of cold water and the pH is brought to 8.4 with 1N aqueous sodium hydroxide. The resulting solution is clarified by filtration and freeze-dried to give N-[6-[4-[(2-dimethylaminoethyl)aminosulfonyl]phenyl]-1,2-dihydro-2-oxonicotinyl]amoxicillin, sodium salt; $[\alpha]_D^{23} = +123°$ (1.03% in 75% dimethylformamide/pyridine); iodometric assay, 71.8%.

EXAMPLE 17

A stirred suspension of 2.02 g. of cephaloglycin hemihydrate in 50 ml. of N,N-dimethylacetamide is cooled to 0°–5° C. and treated in turn with 1.7 ml. of triethylamine and 1.54 ml. of trimethylsilyl chloride. The mixture is stirred at room temperature for 1 hour, then cooled to 0°–5° C. and treated in turn with 0.68 ml. of triethylamine and 1.59 g. of 6-[4-(methylaminosulfonyl)phenyl]-1,2-dihydro-2-oxonicotinyl chloride. The mixture is stirred at 0°–5° C. for 30 minutes, then at room temperature for 16 hours. The mixture is poured into 200 ml. of ice water and the pH is adjusted to 2.1 with dilute hydrochloric acid. The resulting precipitate of N-[6-[4-(methylaminosulfonyl)phenyl]-1,2-dihydro-2-oxonicotinyl]cephaloglycin is collected by filtration, washed well with water and dried. The solid is suspended in 100 ml. of 50% tetrahydrofuran/dimethylformamide and the mixture is treated with 5.0 ml. of 50% sodium 2-ethylhexanoate in n-butanol. The resulting solution is poured into 200 ml. of ether and the precipitated N-[6-[4-(methylaminosulfonyl)phenyl]-1,2-dihydro-2-oxonicotinyl]cephaloglycin, sodium salt is collected by filtration, washed with ether and dried; $[\alpha]_D^{23} = +69°$ (1.02% in methanol); chromatography indicates a purity of 94%.

EXAMPLE 18

By substituting 2.3 g. of 6-[4-[bis(2-hydroxyethyl)aminosulfonyl]phenyl]-1,2-dihydro-2-oxonicotinic acid, 2,5-dioxo1-pyrrolidinyl ester, for the 6-[4-(methylaminosulfonyl)phenyl]-1,2-dihydro-2-oxonicotinyl chloride in Example 17, there is obtained N-[6-[4-[bis(2-hydroxyethyl)aminosulfonyl]phenyl]-1,2-dihydro-2-oxonicotinyl]cephaloglycin. This solid is suspended in 50 ml. of cold water and the pH is brought to 7.5 with 1N aqueous sodium hydroxide. The solution is clarified by filtration and freeze-dried to give N-[6-[4-[bis(2-hydroxyethyl)aminosulfonyl]phenyl]-1,2-dihydro-2-oxonicotinyl]cephaloglycin, sodium salt; $[\alpha]_D^{23} = +70°$; chromatography indicates a purity of 99%.

EXAMPLE 19

A stirred suspension of 2.2 g. of 7-α-methoxycephaloglycin (Brit. Pat. No. 1,348,984) in 30 ml. of N,N-dimethylacetamide is cooled to 0°–5° C. and treated in turn with 1.05 ml. of trimethylsilyl chloride and 1.2 ml. of triethylamine. The mixture is stirred at 0°–5° C. for 10 minutes, then treated in turn with 1.4 g. of 6-[4-(dimethylaminosulfonyl)phenyl]-1,2-dihydro-2-oxonicotinyl chloride and 0.56 ml. of triethylamine. The mixture is stirred for 1 hour at 5° C., filtered and the filtrate treated with 5.0 ml. of 50% sodium 2-ethylhexanoate in n-butanol. The resulting solution is diluted with 100 ml. of ethyl acetate. The precipitate of N-[6-[4-(dimethylaminosulfonyl)phenyl]-1,2-dihydro-2-oxonicotinyl]-7-α-methoxycephaloglycin, sodium salt is collected by filtration, washed with ethyl acetate and dried; $[\alpha]_D^{23} = +42.5°$ (0.99% in pH 7 phosphate buffer); chromatography indicates a purity of 85.5%.

EXAMPLE 20

A stirred solution of 5.2 g. of the sodium salt of 3-[[(5-methyl-1,3,4-thiadiazol-2-yl)thio]methyl]-7-(D-α-amino-α-phenylacetamido)-3-cephem-4-carboxylic acid (U.S. Pat. No. 3,954,734) in 60 ml. of N,N-dimethylacetamide is cooled to 0°–5° C. and treated in turn with 3.04 g. of 6-[4-(dimethylaminosulfonyl)phenyl°-1,2-dihydro-2-oxonicotinyl chloride and 1.37 ml. of triethylamine. The mixture is stirred for 3 hours at 0°–5° C., then poured into 200 ml. of ice water. The pH is adjusted to 3.0 with dilute hydrochloric acid and the resulting precipitate of 3-[[(5-methyl-1,3,4-thiadiazol-2-yl)thio]methyl]-7-[D-α-[6-[4-(dimethylaminosulfonyl)phenyl]-1,2-dihydro-2-oxonicotinamido]-α-phenylacetamido]-3-cephem-4-carboxylic acid is collected by filtration and washed well with water. The solid is suspended in 400 ml. of ice water and the pH is brought to 8.0 with 1N aqueous sodium hydroxide. The solution is clarified by filtration and freeze-dried to give the 3-[[(5-methyl-1,3,4-thiadiazol-2-yl)thio]methyl]-7-[D-α-[6-[4-(dimethylaminosulfonyl)phenyl]-1,2-dihydro-2-oxonicotinamido]-α-phenylacetamido]-3-cephem-4-carboxylic acid, sodium salt; $[\alpha]_D^{23} = -36°$ (1.0% in methanol); chromatography indicates a purity of 78%.

EXAMPLE 21

By substituting 1.7 g. of 6-[4-(dimethylaminosulfonyl)phenyl]-1,2-dihydro-2-oxonicotinyl chloride for the 6-[4-(methylaminosulfonyl)phenyl]-1,2-dihydro-2-oxonicotinyl chloride in Example 17, there is obtained N-[6-[4-(dimethylaminosulfonyl)phenyl]-1,2-dihydro-2-oxonicotinyl]cephaloglycin, sodium salt; $[\alpha]_D^{23} = +71°$ (1.04% in 75% dimethylformamide/pyridine; chromatography indicates a purity of 90%.

EXAMPLE 22

A stirred solution of 5.2 g. of the sodium salt of 3-[[(5-methyl-1,3,4-thiadiazol-2-yl)thio]methyl]-7-(D-α-amino-α-phenyl-acetamido)-3-cephem-4-carboxylic acid in 70 ml. of N,N-dimethyl-acetamide is cooled to 0°–5° and treated with 4.8 g. of 6-[4-[bis-(2-hydroxyethyl)aminosulfonyl]phenyl]-1,2-dihydro-2-oxonicotinic acid, 2,5-dioxo-1-pyrrolidinyl ester. The mixture is stirred at 0°–5° C. for 2.5 hours, then at room temperature for 16 hours. The resulting solution is poured into 250 ml. of ethyl acetate and the precipitated solid collected by filtration, washed with ethyl acetate and dried. The solid is dissolved in 200 ml. of ice water and the pH is adjusted to 2.0 with dilute hydrochloric acid. The resulting precipitate of 3-[[(5-methyl-1,3,4-thiadiazol-2-yl)thio]methyl]-7-[D-α-[6-[4-[bis(2-hydroxyethyl)aminosulfonyl]phenyl]-1,2-dihydro-2-oxonicotinamido]-α-phenylacetamido]-3-cephem-4-carboxylic acid is collected by filtration and washed well with cold water. The solid is suspended in 500 ml. of cold water and the pH brought to 7.7 with 1N aqueous sodium hydroxide. The resulting solution is clarified by filtration and freeze-dried to give 3-[[(5-methyl-1,3,4-thiadiazol-2-yl)thio]methyl]-7-[D-α-[6-[4-[bis(2-hydroxyethyl)aminosulfonyl]phenyl]-1,2-dihydro-2-oxonicotinamido]-α-phenylacetamido]-3-cephem-4-carboxylic acid, sodium salt; $[\alpha]_D^{23} = -8°$ (1% in methanol); chromatography indicates a purity of 77%.

EXAMPLE 23

By substituting 15.2 g. of epicillin hemihydrate for the amoxicillin-dimethyl sulfoxide complex in Example 1, there is obtained N-[6-[4-[bis(2-hydroxyethyl)aminosulfonyl]phenyl]-1,2-dihydro-2-oxonicotinyl]epicillin, sodium salt.

EXAMPLE 24

By substituting 1.79 g. of cephalexin monohydrate for the cephaloglycin hemihydrate in Example 17, there is obtained N-[6-[4-[bis(2-hydroxyethyl)aminosulfonyl]phenyl]-1,2-dihydro-2-oxonicotinyl]cephalexin, sodium salt.

EXAMPLE 25

By substituting an equivalent amount of the sodium salt of the appropriate 3-[[heterocyclic)thio]methyl]-7-(D-α-amino-α-phenylacetamido)-3-cephem-4-carboxylic acid [J. Antibiotics, 29, 65–80 (1976)] for the sodium salt of 3-[[(5-methyl-1,3,4-thiadiazol-2-yl)thio]methyl]-7-(D-α-amino-α-phenylacetamido)-3-cephem-4-carboxylic acid in Example 22, the following products are obtained:

(a) 3-[[(1,2,3-triazol-5-yl)thio]methyl]-7-[D-α-[6-[4-[bis(2-hydroxyethyl)aminosulfonyl]phenyl]-1,2-dihydro-2-oxonicotinamido]-α-phenylacetamido]-3-cephem-4-carboxylic acid, sodium salt.

(b) 3-[[(1,2,3-triazol-5-yl)thio]methyl]-7-[D-α-[6-[4-[bis(2-hydroxyethyl)aminosulfonyl]phenyl]-1,2-dihydro-2-oxonicotinamido]-α-(4-hydroxyphenyl)acetamido]-3-cephem-4-carboxylic acid, sodium salt.

(c) 3-[[(1-methyl-1,2,3,4-tetrazol-5-yl)thio]methyl]-7-[D-α-[6-[4-[bis(2-hydroxyethyl)aminosulfonyl]phenyl]-1,2-dihydro-2-oxonicotinamido-α-phenylacetamido]-3-cephem-4-carboxylic acid, sodium salt.

(d) 3-[[(1-methyl-1,2,3,4-tetrazol-5-yl)thio]methyl]-7-[D-α-[6-[4-[bis(2-hydroxyethyl)aminosulfonyl]phenyl]-1,2-dihydro-2-oxonicotinamido]-α-(4-hydroxyphenyl)acetamido]-3-cephem-4-carboxylic acid, sodium salt.

(e) 3-[[(1-methyl-1,2,3-triazol-5-yl)thio]methyl]-7-[D-α-[6-[4-[bis(2-hydroxyethyl)aminosulfonyl]phenyl]-1,2-dihydro-2-oxonicotinamido]-α-phenylacetamido]-3-cephem-4-carboxylic acid, sodium salt.

(f) 3-[[(4-methyl-1,2,3-triazol-5-yl)thio]methyl]-7-[D-α-[6-[4-[bis(2-hydroxyethyl)aminosulfonyl]phenyl]-1,2-dihydro-2-oxonicotinamido]-α-phenylacetamido]-3-cephem-4-carboxylic acid, sodium salt.

(g) 3-[[(5-methyl-4,1,2-triazol-3-yl)thio]methyl]-7-[D-α-[6-[4-[bis(2-hydroxyethyl)aminosulfonyl]phenyl]-1,2-dihydro-2-oxonicotinamido]-α-phenylacetamido]-3-cephem-4-carboxylic acid, sodium salt.

(h) 3-[[(5-methyl-1,3,4-thiadiazol-2-yl)thio]methyl]-7-[D-α-[6-[4-[bis(2-hydroxyethyl)aminosulfonyl]phenyl]-1,2-dihydro-2-oxonicotinamido]-α-(4-hydroxyphenyl)acetamido]-3-cephem-4-carboxylic acid, sodium salt.

EXAMPLE 26

A stirred solution of 4.55 g. of D-N-[6-[4-(dimethylaminosulfonyl)phenyl]-1,2-dihydro-2-oxonicotinyl]-2-phenylglycine in 50 ml. of N,N-dimethylacetamide is cooled to 0°–5° C. and treated in turn with 1.4 ml. of triethylamine and 0.96 ml. of ethyl chloroformate. The mixture is stirred for 15 minutes at 0°–5° C., then treated with 25 ml. of a 0.44M solution of 6-aminopenicillanic acid, trimethylsilyl ester [Glombitza, Ann. 673,166 (1964)]. The mixture is stirred at 0°–5° C. for 1 hour, then at room temperature for 2 hours. The mixture is poured into 200 ml. of ice water and the pH is adjusted to 2.0 with dilute hydrochloric acid. The resulting precipitate of N-[6-[4-(dimethylaminosulfonyl)phenyl]-1,2-dihydro-2-oxonicotinyl]ampicillin is collected by filtration and washed well with cold water. The solid is suspended in 200 ml. of cold water and the pH is brought to 7.5 with 1N aqueous sodium hydroxide. The resulting solution is clarified by filtration and freeze-dried to give N-[6-[4-(dimethylaminosulfonyl)phenyl]-1,2-dihydro-2-oxonicotinyl]ampicillin, sodium salt; $[\alpha]_D^{23} = +152°$ (1% in methanol).

EXAMPLE 27

By substituting 20 g. of 6-[4-[bis(2-hydroxyethyl)aminosulfonyl]phenyl]-1,2-dihydro-1-methyl-2-oxonicotinic acid, 2,5-dioxo-1-pyrrolidinyl ester for the 20 g. of 6-[4-[bis(2-hydroxyethyl)aminosulfonyl]phenyl]-1,2-dihydro-2-oxonicotinic acid, 2,5-dioxo-1-pyrrolidinyl ester of Example 1, there is obtained N-[6-[4-bis(2-hydroxyethyl)aminosulfonyl]phenyl]-1,2-dihydro-1-methyl-2-oxonicotinyl]amoxicillin, sodium salt.

EXAMPLE 28

By substituting 14.2 g. of 6-[4-(dimethylaminosulfonyl)phenyl]-1,2-dihydro-1-methyl-2-oxonicotinyl chloride for the 20 g. of 6-[4-[bis(2-hydroxyethyl)aminosulfonyl]phenyl]-1,2-dihydro-2-oxonicotinic acid, 2,5-dioxo-1-pyrrolidinyl ester of Example 1, there is obtained N-[6-[4-(dimethylaminosulfonyl)phenyl]-1,2-dihydro-1-methyl-2-oxonicotinyl]amoxicillin, sodium salt.

STARTING MATERIALS AND INTERMEDIATES

A. Amoxicillin-Dimethyl Sulfoxide Complex

Fifty grams of amoxicillin trihydrate is added in portions, with stirring, to 375 ml. of dimethyl sulfoxide. The mixture is stirred at room temperature for 2 hours, then diluted with 75 ml. of methylene chloride and cooled to 0°–5°. The solid product is collected by filtration, washed with methylene chloride and dried. Analysis shows 3 moles of dimethyl sulfoxide and 0.5 mole of water for each mole of amoxicillin; formula weight = 609.

B. 4-Acetylbenzenesulfonyl Chloride

A suspension of 100 g. of sodium 4-acetylbenzenesulfonate in 225 ml. of dimethylformamide is treated with 31 ml. of thionyl chloride and the mixture is stirred at room temperature for 5 minutes, then poured into 1 l. of ice water. The resulting precipitate of 4-acetylbenzenesulfonyl chloride is collected by filtration and washed with ice water. The still-damp product may be used as such without further purification. However, if purification is desired, the following procedure may be used: The product is dissolved in methylene chloride and the solution is dried and evaporated at reduced pressure. Th residual sulfonyl chloride is crystallized from benzene/hexane; m.p. 83°–85° C.

C. 4-Acetylbenzenesulfonamides

(a) 4-Acetyl-N,N-bis(2-hydroxyethyl)benzenesulfonamide

The damp 4-acetylbenzenesulfonyl chloride from 300 g. of sodium 4-acetylbenzenesulfonate is added in portions to a well-stirred, cooled solution of 500 ml. of bis(2-hydroxyethyl)amine in 750 ml. of water. The mixture is stirred at room temperature for 16 hours, cooled to 0°–5° C. and the precipitate of 4-acetyl-N,N-bis(2-hydroxyethyl)benzenesulfonamide is collected by filtration and crystallized from water; m.p. 87.5°–89.5° C.

(b) 4-Acetyl-N-methylbenzenesulfonamide

The damp 4-acetylbenzenesulfonyl chloride from 50 g. of sodium 4-acetylbenzenesulfonate is added in portions, with stirring, to 500 ml. of cold 40% aqueous methylamine. The mixture is stirred at room temperature for 16 hours, then cooled and the precipitate collected by filtration. The solid (which proved to be the N-methylimine derivative of the ketosulfonamide) is dissolved in 300 ml. of 6% hydrochloric acid and the solution is heated at 80°–90° C. for 30 minutes, then cooled. The resulting precipitate of 4-acetyl-N-methylbenzenesulfonamide is collected by filtration and crystallized from aqueous ethanol; m.p. 107°–109° C.

(c) 4-Acetylbenzenesulfonamide

The damp 4-acetylbenzenesulfonyl chloride from 50 g. of sodium 4-acetylbenzenesulfonate is added in portions, with stirring, to 500 ml. of concentrated aqueous ammonia. The mixture is stirred at room temperature for 16 hours, cooled, and the precipitated 4-acetylbenzenesulfonamide removed by filtration and crystallized from aqueous ethanol/acetone; m.p. 177°–179° C.

(d) 4-Acetyl-N,N-dimethylbenzenesulfonamide

From the damp 4-acetylbenzenesulfonyl chloride from 200 g. of sodium 4-acetylbenzenesulfonate, and 1 l. of 20% aqueous dimethylamine, following the procedure of (c) above, there is obtained 4-acetyl-N,N-dimethylbenzenesulfonamide; m.p. 97°–99° C. after crystallization from aqueous ethanol.

(e) 4-Acetyl-N-(3-pyridyl)benzenesulfonamide

To a solution of 23.7 g. of 3-aminopyridine in 400 ml. of pyridine is added 55 g. of 4-acetylbenzenesulfonyl chloride and the resulting solution is stirred at room temperature for 24 hours. The solution is poured into 1 l. of water and the mixture is cooled to 0°–5° C. The precipitate of 4-acetyl-N-(3-pyridyl)benzenesulfonamide is collected by filtration, washed with water and dried; m.p. 182°–183° after crystallization from ethanol.

(f) 4-Acetyl-N-(2-pyridyl)benzenesulfonamide

A solution of 13.4 g. of 2-aminopyridine in 300 ml. of pyridine is treated with 31.0 g. of 4-acetylbenzenesulfonyl chloride and the solution is stirred at room temperature for 6 hours. The solution is poured into 1 l. of cold water and the resulting precipitate of 4-acetyl-N-(2-pyridyl)benzensulfonamide is collected by filtration, washed with water and dried; m.p. 201°–202° C. after crystallization from methanol.

(g) 1-(4-Acetylbenzenesulfonyl)pyrrolidine

A solution of 500 ml. of 50% aqueous pyrrolidine is treated in portions with 30.0 g. of 4-acetylbenzenesulfonyl chloride and the solution is stirred at room temperature for 1 hour. The resulting mixture is cooled to 0°–5° C. and the precipitated 1-(4-acetylbenzenesulfonyl)pyrrolidine is collected by filtration, washed with water and dried; m.p. 138°–139° C. after crystallizations from aqueous methanol and from 2-propanol.

(h) 1-(4-Acetylbenzenesulfonyl)piperidine

The damp 4-acetylbenzenesulfonyl chloride from 100 g. of sodium 4-acetylbenzenesulfonate is added to a stirred solution of 500 ml. of 50% aqueous piperidine. The mixture is stirred at room temperature for 16 hours, cooled, and the precipitated 1-(4-acetylbenzenesulfonyl)piperidine removed by filtration, washed with water and dried; m.p. 113°–114° C. after crystallization from 2-propanol.

(i) 4-Acetyl-N,N-diethylbenzenesulfonamide

The damp 4-acetylbenzenesulfonyl chloride from 100 g. of sodium 4-acetylbenzenesulfonate is added to a stirred solution of 500 ml. of 50% aqueous diethylamine. The mixture is stirred at room temperature for 4 hours, cooled, and the precipitated 4-acetyl-N,N-diethylbenzenesulfonamide removed fy filtration, washed with water and dried; m.p. 78°–79° C. after crystallization from 2-propanol.

(j) 4-Acetyl-N-(2-hydroxyethyl)benzenesulfonamide

The damp 4-acetylbenzenesulfonyl chloride from 100 g. of sodium 4-acetylbenzenesulfonate is added to a stirred solution of 500 ml. of 50% aqueous 2-hydroxyethylamine. The mixture is stirred at room temperature for 16 hours, then acidified with hydrochloric acid and cooled to 0°–5° C. The precipitate of 4-acetyl-N-(2-hydroxyethyl)benzenesulfonamide is collected by filtration, washed with water and dried; m.p. 119°–121° C. after crystallization from water.

(k) 1-(4-Acetylbenzenesulfonyl)-3-piperidinemethanol

The damp 4-acetylbenzenesulfonyl chloride from 100 g. of sodium 4-acetylbenzenesulfonate is added to a solution of 114 g. of 3-piperidinemethanol in 900 ml. of water. The mixture is stirred at room temperature for 16 hours, cooled, and the precipitate for 1-(4-acetylbenzenesulfonyl)-3-piperidinemethanol collected by filtration, washed with water and dried; m.p. 104°–106° C. after crystallization from aqueous ethanol.

(l) 4-Acetyl-N-(2-dimethylaminoethyl)benzenesulfonamide

The damp 4-acetylbenzenesulfonyl chloride from 100 g. of sodium 4-acetylbenzenesulfonate is added to a solution of 83 g. of N,N-dimethylethylenediamine in 730 ml. of water. The mixture is stirred at room temperature for 16 hours, cooled, and the precipitate of 4-acetyl-N-(2-dimethylaminoethyl)benzenesulfonamide collected by filtration, washed with water and dried; m.p. 87°–89° C. after crystallization from 2-propanol/hexane.

D.
6-(Substituted-phenyl)-1,2-dihydro-2-oxonicotinonitriles

(a)
6-[4-[Bis(2-hydroxyethyl)aminosulfonyl]phenyl-1,2-dihydro-2-oxonicotinonitrile A stirred suspension of 117.7 g. of sodium methoxide in 1 l. of tetrahydrofuran under a nitrogen atmosphere is cooled to 0°–5° C. and treated with 178 ml. of ethyl formate. The cold mixture is then treated dropwise, with stirring, with a solution of 190.1 g. of 4-acetyl-N,N-bis(2-hydroxyethyl)benzenesulfonamide in 1.75 l. of tetrahydrofuran, then stirred at room temperature for 16 hours. The mixture is diluted with 500 ml. of ether and the resulting precipitate of the sodium salt of 4-[bis(2-hydroxyethyl)aminosulfonyl]benzoylacetaldehyde is collected by filtration, washed with ether and dried. A solution of this sodium salt in 2.5 l. of water is adjusted to pH 9 with acetic acid and 84 g. of cyanoacetamide is added. The solution is heated at 90° for 6 hours, then allowed to stand at room temperature for 16 hours. The mixture is acidified to pH 6 with acetic acid and cooled to 0°–5°. The resulting precipitate of 6-[4-[bis(2-hydroxyethyl)aminosulfonyl]phenyl]-1,2-dihydro-2-oxonicotinonitrile is collected by filtration, washed with water and dried; m.p. 226°–228° C. after crystallization from aqueous methanol/dimethylformamide.

In a similar manner, the following nitriles are prepared:

(b)
6-[3-(Aminosulfonyl)phenyl]-1,2-dihydro-2-oxonicotinitrile

From a solution of the sodium salt of 3-(aminosulfonyl)benzoylacetaldehyde in 1 l. of water (prepared from 20.5 g. of sodium methoxide in 500 ml. of tetrahydrofuran, 31 ml. of ethyl formate, and a solution of 34.0 g. of 3-acetylbenzenesulfonamide [J. prakt. Chem., 22, 192 (1963)] in 500 ml. of tetrahydrofuran) and 21.8 g. of cyanoacetamide, there is obtained 6-[3-(aminosulfonyl)-phenyl]-1,2-dihydro-2-oxonicotinonitrile; m.p. 271°–274° C. (dec.) after digestion with ethyl acetate.

(c)
6-[4-(Methylaminosulfonyl)phenyl]-1,2-dihydro-2-oxonicotinonitrile From a solution of the sodium salt of 4-(methylaminosulfonyl)benzoylacetaldehyde in 1 l. of water (prepared from 25.3 g. of sodium methoxide in 500 ml. of tetrahydrofuran, 38.2 ml. of ethyl formate, and a solution of 45.4 g. of 4-acetyl-N-methylbenzenesulfonamide in 700 ml. of tetrahydrofuran) and 26.8 g. of cyanoacetamide, there is obtained 6-[4-(methylaminosulfonyl)phenyl]-1,2-dihydro-2-oxonicotinonitrile; m.p. 282°–286° C. (dec.) after crystallization from aqueous dimethylformamide.

(d)
6-[4-(Aminosulfonyl)phenyl]-1,2-dihydro-2-oxonicotinonitrile

From a solution of the sodium salt of 4-(aminosulfonyl)benzoylacetaldehyde in 1.5 l. of water (prepared from 28.6 g. of sodium methoxide in 500 ml. of tetrahydrofuran, 43 ml. of ethyl formate, and a solution of 48 g. of 4-acetylbenzenesulfonamide in 1 l. of tetrahydrofuran) and 30.2 g. of cyanoacetamide, there is obtained 6-[4-(aminosulfonyl)phenyl]-1,2-dihydro-2-oxonicotinonitrile; m.p. 267°–268° C. (dec.) after digestion with hot ethyl acetate.

(e)
6-[4-(Dimethylaminosulfonyl)phenyl]-1,2-dihydro-2-oxonicotinonitrile From a solution of the sodium salt of 4-(dimethylaminosulfonyl)benzoylacetaldehyde in 2 l. of water (prepared from 36.1 g. of sodium methoxide in 500 ml. of tetrahydrofuran, 49.5 g. of ethyl formate, and a solution of 137.8 g. of 4-acetyl-N,N-dimethylbenzenesulfonamide in 1.4 l. of tetrahydrofuran) and 76.6 g. of cyanoacetamide, there is obtained 6-[4-dimethylaminosulfonyl)phenyl]-1,2-dihydro-2-oxonicotinonitrile; m.p. 263°–267° C. (dec.) after crystallization from aqueous dimethylformamide.

(f)
6-[4-(2-Pyridylaminosulfonyl)phenyl]-1,2-dihydro-2-oxonicotinonitrile From a solution of the sodium salt of 4-(3-pyridylaminosulfonyl)benzoylacetaldehyde in 1 l. of water (prepared from 17.3 g. of sodium methoxide in 300 ml. of tetrahydrofuran, 26 ml. of ethyl formate, and a solution of 42 g. of 4-acetyl-N-(3-pyridyl)benzenesulfonamide in 1 l. of tetrahydrofuran) and 19.2 g. of cyanoacetamide, there is obtained 6-[4-(3-pyridylaminosulfonyl)phenyl]-1,2-dihydro-2-oxonicotinonitrile; m.p. 237°–239° C. after digestion with warm methanol and with warm ethyl acetate.

(g)
6-[4-(2-Pyridylaminosulfonyl)phenyl]-1,2-dihydro-2-oxonicotinonitrile From a solution of the sodium salt of 4-(3-pyridylaminosulfonyl)benzoylacetaldehyde in 400 ml. of water (prepared from 7.85 g. of sodium methoxide in 400 ml. of tetrahydrofuran, 11.8 ml. of ethyl formate, and a solution of 19.0 g. of 4-acetyl-N-(2-pyridyl)benzenesulfonamide in 400 ml. of tetrahydrofuran) and 8.75 g. of cyanoacetamide, there is obtained 6-[4-(2-pyridylaminosulfonyl)phenyl]-1,2-dihydro-2-oxonicotinonitrile; m.p. 254°–255° C. after crystallization from aqueous ethanol/dimethylformamide.

(h)
6-[4-(1-Pyrrolidinylsulfonyl)phenyl]-1,2-dihydro-2-oxonicotinonitrile From a solution of the sodium salt of 4-(1-pyrrolidinylsulfonyl)benzoylacetaldehyde in 400 ml. of water (prepared from 3.82 g. of sodium methoxide in 200 ml. of tetrahydrofuran, 5.8 ml. of ethyl formate, and a solution of 16.3 g. of 1-(4-acetylbenzenesulfonyl)pyrrolidine in 200 ml. of tetrahydrofuran) and 8.2 g. of cyanoacetamide, there is obtained 6-[4-(1-pyrrolidinylsulfonyl)phenyl]-1,2-dihydro-2-oxonicotinonitrile; m.p. 298°–301° C. (dec.) after crystallization from aqueous dimethylformamide.

(i)
6-[4-(1-Piperidinylsulfonyl)phenyl]-1,2-dihydro-2-oxonicotinonitrile From a solution of the sodium salt of 4-(1-piperidinylsulfonyl)benzoylacetaldehyde in 400 ml. of water (prepared from 8.9 g. of sodium methoxide in 300 ml. of tetrahydrofuran, 13.4 ml. of ethyl formate, and a solution of 40.0 g. of 1-(4-acetyl-benzenesulfonyl)piperidine in 400 ml. of tetrahydrofuran) and 18.9 g. of cyanoacetamide, there is obtained 6-[4-(1-piperidinylsulfonyl)phenyl]-1,2-dihydro-2-oxonicotinonitrile; m.p. 312°–314° C. after crystallization from methanol-dimethylformamide.

(j)
6-[4-(Diethylaminosulfonyl)phenyl]-1,2-dihydro-2-oxonicotinonitrile

From a solution of the sodium salt of 4-(diethylaminosulfonyl)benzoylacetaldehyde in 500 ml. of water (prepared from 9.34 g. of sodium methoxide in 300 ml. of tetrahydrofuran, 14.1 ml. of ethyl formate, and a solution of 40.0 g. of 4-acetyl-N,N-diethylbenzenesulfonamide in 300 ml. of tetrahydrofuran) and 19.7 g. of cyanoacetamide, there is obtained 6-[4-(diethylaminosulfonyl)phenyl]-1,2-dihydro-2-oxonicotinonitrile; m.p. 232°–234° C. after crystallization from aqueous dimethylformamide.

(k)
6-[4-[(2-Hydroxyethyl)aminosulfonyl]phenyl]-1,2-dihydro-2-oxonicotinonitrile From a solution of the sodium salt of 4-[(2-hydroxyethyl)aminosulfonyl]benzoylacetaldehyde in 500 ml. of water (prepared from 41.3 g. of sodium methoxide in 400 ml. of tetrahydrofuran, 56.6 g. of ethyl formate, and a solution of 56.5 g. of 4-acetyl-N-(2-hydroxyethyl)benzenesulfonamide in 700 ml. of tetrahydrofuran) and 29.7 g. of cyanoacetamide, there is obtained 6-[4-[(2-hydroxyethyl)aminosulfonyl]phenyl]-1,2-dihydro-2-oxonicotinonitrile; m.p. 283°–286° C. after crystallization from methanol-dimethylformamide.

(l)
6-[4-(3-Hydroxymethyl-1-piperidinylsulfonyl)phenyl]-1,2-dihydro-2-oxonicotinonitrile From a solution of the sodium salt of 4-(3-hydroxymethyl-1-piperidinylsulfonyl)benzoylacetaldehyde in 1 l. of water (prepared from 26.6 g. of sodium methoxide in 250 ml. of tetrahydrofuran, 36.5 g. of ethyl formate, and a solution of 66.5 g. of 1-(4-acetyl-benzenesulfonyl)-3-piperidinemethanol in 600 ml. of tetrahydrofuran) and 28.2 g. of cyanoacetamide, there is obtained 6-[4-(3-hydroxymethyl-1-piperidinylsulfonyl)phenyl]-1,2-dihydro-2-oxonicotinonitrile; m.p. 269°–272° C. after crystallization from aqueous dimethylformamide.

(m)
6-[4-[(2-Dimethylaminoethyl)aminosulfonyl]phenyl]-1,2-dihydro-2-oxonicotinonitrile From a solution of the sodium salt of 4-[(2-dimethylaminoethyl)aminosulfonyl]benzoylacetaldehyde in 1 l. of water (prepared from 23.7 g. of sodium methoxide in 240 ml. of tetrahydrofuran, 32.5 g. of ethyl formate, and a solution of 53.9 g. of 4-acetyl-N-(2-dimethylaminoethyl)benzenesulfonamide in 540 ml. of tetrahydrofuran) and 25.1 g. of cyanoacetamide, there is obtained 6-[4-[(2-dimethylaminoethyl)aminosulfonyl]phenyl]-1,2-dihydro-2-oxonicotinonitrile; m.p. 269°–272° C. (dec.) after crystallization from dimethylformamide/2-propanol.

(n)
6-[4-[bis(2-hydroxyethyl)aminosulfonyl]phenyl]-1,2-dihydro-1-methyl-2-oxonicotinonitrile A stirred suspension of 117.7 g. of sodium methoxide in 1 l. tetrahydrofuran and under nitrogen is cooled in ice and treated with 178 ml. of ethylformate. The cold mixture is treated dropwise with stirring, with a solution of 190.1 g. of 4-acetyl-N,N-bis(2-hydroxyethyl)benzenesulfonamide in 1.75 l. tetrahydrofuran, then stirred at room temperature for 16 hours. The mixture is diluted with 500 ml. of ether and the resulting precipitate of the sodium salt of 4-[bis(2-hydroxyethyl)aminosulfonyl]benzoylacetaldehyde is collected by filtration, washed with ether, and dried. A solution of this sodium salt in 2.5 l. water is adjusted to pH 9 with acetic acid and 98 g. of N-methylcyanoacetamide is added. The solution is heated to 90° C. for 6 hours, then allowed to stand at room temperature for 16 hours. The mixture is acidified to pH 6 with acetic acid and cooled to 0°–5°. The resulting precipitate of 6-[4-[bis(2-hydroxyethyl)aminosulfonyl]phenyl]-1,2-dihydro-1-methyl-2-oxonicotinonitrile is collected by filtration, washed with water, and dried. Recrystallization from dimethylformamide/water gives the pure product.

(o)
6-[(4-dimethylaminosulfonyl)phenyl]-1,2-dihydro-1-methyl-2-oxonicotinonitrile From a solution of the sodium salt of 4-(dimethylaminosulfonyl)-benzoylacetaldehyde in 2 l. water (prepared from 36.1 g. sodium methoxide in 500 ml. tetrahydrofuran, 49.5 g. of ethylformate, and a solution of 137.8 g. of 4-acetyl-N,N-dimethylbenzenesulfonamide in 1.4 l. of tetrahydrofuran) and 89.3 g. of N-methylcyanoacetamide, there is obtained 6-[(4-dimethylaminosulfonyl)phenyl]-1,2-dihydro-1-methyl-2-oxonicotinonitrile. Recrystallization from dimethylformamide/water gives the pure product.

E. 6-(Substituted-phenyl)-1,2-dihydro-2-oxonicotinic Acids

(a)
6-[4-[Bis(2-hydroxyethyl)aminosulfonyl]phenyl]-1,2-dihydro 2-oxonicotinic Acid A mixture of 80 g. of 6-[4-[bis(2-hydroxyethyl)aminosulfonyl]phenyl]-1,2-dihydro-2-oxonicotinonitrile and 2.4 l. of 5% aqueous sodium hydroxide is heated at reflux in a stainless steel flask for 40 hours. The resulting solution is cooled and acidified with hydrochloric acid. The precipitate of 6-[4-[bis(2-hydroxyethyl)aminosulfonyl]phenyl]-1,2-dihydro-2-oxonicotinic acid is collected by filtration, washed with water and dried; m.p. 252°–254° C. after crystallization from aqueous methanol/dimethylformamide.

In a similar manner, the following acids are prepared by hydrolysis of the corresponding nitrile with 5% aqueous sodium hydroxide, followed by acidification of the reaction mixture:

(b)
6-[3-(Aminosulfonyl)phenyl]-1,2-dihydro-2-oxonicotinic Acid

M.P. 298–300° C. (dec.) from aqueous dimethylformamide.

(c)
6-[4-(Methylaminosulfonyl)phenyl]-1,2-dihydro-2-oxonicotinic Acid

M.P. 278°–280° C. (dec.) from aqueous dimethylformamide.

(d)
6-[4-(Aminosulfonyl)phenyl]-1,2-dihydro-2-oxonicotinic Acid

M.P. 290°–291° C. (dec.) from aqueous dimethylformamide.

(e)
6-[4-(Dimethylaminosulfonyl)phenyl]-1,2-dihydro-2-oxonicotinic Acid

M.P. 275°–277° C. (dec.) from aqueous dimethylformamide.

(f)
6-[4-(3-Pyridylaminosulfonyl)phenyl]-1,2-dihydro-2-oxonicotinic Acid

The product is precipitated at pH 4.4 with acetic acid; m.p. 278°–279° C. (dec.) from aqueous dimethylformamide.

(g)
6-[4-(2-Pyridylaminosulfonyl)phenyl]-1,2-dihydro-2-oxonicotinic Acid

The product is precipitated at pH 4.3 with acetic acid; m.p. 282°–283° C. (dec.) from aqueous ethanolic dimethylformamide.

(h)
6-[4-(Pyrrolidinylsulfonyl)phenyl]-1,2-dihydro-2-oxonicotinic Acid

M.P. 292°–294° C. (dec.) from aqueous dimethylformamide.

(i)
6-[4-(1-Piperidinylsulfonyl)phenyl]-1,2-dihydro-2-oxonicotinic Acid

M.P. 300°–302° C. (dec.) from ethanolic dimethylformamide.

(j)
6-[4-(Diethylaminosulfonyl)phenyl]-1,2-dihydro-2-oxonicotinic Acid

M.P. 228°–229° C. from 2-propanol/dimethylformamide.

(k)
6-[4-[(2-Hydroxyethyl)aminosulfonyl]phenyl]-1,2-dihydro-2-oxonicotinic Acid M.P. 290°–295° C. (dec.) from aqueous dimethylformamide.

(l)
6-[4-(3-Hydroxymethyl-1-piperidinylsulfonyl)phenyl]-1,2-dihydro-2-oxonicotinic Acid M.P. 300°–304° C. from ethanolic dimethylformamide.

(m)
6-[4-[(2-Dimethylaminoethyl)aminosulfonyl]phenyl]-1,2-dihydro-2-oxonicotinic Acid The product is precipitated at pH 4.5 with dilute hydrochloric acid; m.p. 277°–278° C. (dec.) from ethanolic dimethylformamide.

(n)
6-[4-[Bis(2-hydroxyethyl)aminosulfonyl]phenyl]-1,2-dihydro-1-methyl-2-oxonicotinic Acid

(o)
6-[(4-Dimethylaminosulfonyl)phenyl]-1,2-dihydro-1-methyl-2-oxonicotinic Acid

F. 6-(Substituted-phenyl)-1,2-dihydro-2-oxonicotinyl Chlorides

(a)
6-[3-(Aminosulfonyl)phenyl]-1,2-dihydro-2-oxonicotinyl Chloride

A stirred suspension of 2.6 g. of 6-[3-(aminosulfonyl)phenyl]-1,2-dihydro-2-oxonicotinic acid in 130 ml. of tetrahydrofuran is treated with 1.24 ml. of triethylamine. After a few minutes, the resulting solution is treated with 1.12 ml. of trimethylsilyl chloride and stirred 1 hour at room temperature. The solution is then treated with 1.28 ml. of thionyl chloride and stirred for 2 hours at room temperature. The resulting solution is diluted with 200 ml. of hexane and the precipitate of 6-[3-aminosulfonyl)phenyl]-1,2-dihydro-2-oxonicotinyl chloride is collected by filtration, washed with hexane and dried. The acid chloride is used as such without further purification.

(b)
6-[4-(Methylaminosulfonyl)phenyl]-1,2-dihydro-2-oxonicotinyl Chloride

From 5.0 g. of 6-[4-(methylaminosulfonyl)phenyl]-1,2-dihydro-2-oxonicotinic acid in 250 ml. of tetrahydrofuran, 2.26 ml. of triethylamine, 2.05 ml. of trimethylsilyl chloride and 2.33 ml. of thionyl chloride, following the procedure of a) above, there is obtained 6-[4-(methylaminosulfonyl)phenyl]-1,2-dihydro-2-oxonicotinyl chloride.

(c)
6-[4-(Aminosulfonyl)phenyl]-1,2-dihydro-2-oxonicotinyl Chloride

A suspension of 4.0 g. of 6-[4-(aminosulfonyl)phenyl]-1,2-dihydro-2-oxonicotinic acid in 120 ml. of thionyl chloride is treated with 1 ml. of dimethylformamide and stirred at room temperature for 4 hours. The mixture is diluted with 200 ml. of hexane and the precipitate of 6-[4-(aminosulfonyl)phenyl]-1,2-dihydro-2-oxonicotinyl chloride is collected, washed with hexane and dried. The acid chloride is used as such without further purification.

(d)
6-[4-(Dimethylaminosulfonyl)phenyl]-1,2-dihydro-2-oxonicotinyl Chloride

From 3.5 g. of 6-[dimethylaminosulfonyl)phenyl]-1,2-dihydro-2-oxonicotinic acid in 120 ml. of methylene chloride, 1.55 ml. of triethylamine, 1.4 ml. of trimethylsilyl chloride and 1.6 ml. of thionyl chloride, following the procedure of a) above, there is obtained 6-[4-(dimethylaminosulfonyl)phenyl]-1,2-dihydro-2-oxonicotinyl chloride.

(e)
6-[4-(3-Pyridylaminosulfonyl)phenyl]-1,2-dihydro-2-oxonicotinyl Chloride Hydrochloride From 4.0 g. of 6-[4-(3-pyridylaminosulfonyl)phenyl]-1,2-dihydro-2-oxonicotinic acid in 150 ml. of methylene chloride, 1.55 ml. of trimethylamine, 1.4 ml. of trimethylsilyl chloride and 1.6 ml. of thionyl chloride, following the procedure of (a) above, there is obtained 6-[4-(3-pyridylaminosulfonyl)phenyl]-1,2-dihydro-2-oxonicotinyl chloride hydrochloride.

(f)
6-[4-(2-Pyridylaminosulfonyl)phenyl]-1,2-dihydro-2-oxonicotinyl Chloride Hydrochloride From 7.0 g. of 6-[4-(2-pyridylaminosulfonyl)phenyl]-1,2-dihydro-2-oxonicotinic acid in 200 ml. of thionyl chloride, and 1.5 ml. of dimethylformamide, following the procedure of (c) above, there is obtained 6-[4-(2-pyridylaminosulfonyl)phenyl]-1,2-dihydro-2-oxonicotinyl chloride hydrochloride.

(g)
6-[4-(1-Pyrrolidinylsulfonyl)phenyl]-1,2-dihydro-2-oxonicotinyl Chloride From 4.4 g. of 6-[4-(1-pyrrolidinylsulfonyl)phenyl]-1,2-dihydro-2-oxonicotinic acid in 150 ml. of methylene chloride, 1.6 ml. of triethylamine, 1.45 ml. of trimethylsilyl chloride and 1.7 ml. of thionyl chloride, following the procedure of a) above, there is obtained 6-[4-(1-pyrrolidinylsulfonyl)phenyl]-1,2-dihydro-2-oxonicotinyl chloride.

(h)
6-[4-(1-Piperidinylsulfonyl)phenyl]-1,2-dihydro-2-oxonicotinyl Chloride From 5.0 g. of 6-[4-(1-piperidinylsulfonyl)phenyl]-1,2-dihydro-2-oxonicotinic acid in 150 ml. of methylene chloride, 2.0 ml. of triethylamine, 1.75 ml. of trimethylsilyl chloride and 2.0 ml. of thionyl chloride, following the procedure of a) above, there is obtained 6-[4-(1-piperidinylsulfonyl)phenyl]-1,2-dihydro-2-oxonicotinyl chloride.

(i)
6-[4-(Diethylaminosulfonyl)phenyl]-1,2-dihydro-2-oxonicotinyl Chloride From 6.0 g. of 6-[4-(diethylaminosulfonyl)phenyl]-1,2-dihydro-2-oxonicotinic acid in 175 ml. of methylene chloride, 2.4 ml. of triethylamine, 2.2 ml. of trimethylsilyl chloride and 2.5 ml. of thionyl chloride, following the procedure of a) above, there is obtained 6-[4-(diethylaminosulfonyl)phenyl]-1,2-dihydro-2-oxonicotinyl chloride.

(j)
6-[4-[(2-Dimethylaminoethyl)aminosulfonyl]phenyl]-1,2-dihydro-2-oxonicotinyl Chloride Hydrochloride A suspension of 3.5 g. of 6-[4-[(2-dimethylaminoethyl)aminosulfonyl]phenyl]-1,2-dihydro-2-oxonicotinic acid in 175 ml. of thionyl chloride is stirred at room temperature for 16 hours. The mixture is diluted with 300 ml. of hexane and the precipitate of 6-[4-[(2-dimethylaminoethyl)aminosulfonyl]phenyl]-1,2-dihydro-2-oxonicotinyl chloride hydrochloride is collected by filtration, washed with hexane and dried. The acid chloride is used as such without further purification.

(k)
6-[(4-dimethylaminosulfonyl)phenyl]-1,2-dihydro-1-methyl-2-oxonicotinyl Chloride Utilizing the procedure of part F, a) but using 6-[(4-dimethylaminosulfonyl)phenyl]-1,2-dihydro-1-methyl-2-oxonicotinic acid in place of 6-[3-(aminosulfonyl)phenyl]-1,2-dihydro-2-oxonicotinic acid, the above named product is obtained.

G. 2,5-Dioxo-1-pyrrolidinyl Esters of 1,2-Dihydro-2-oxonicotinic Acids

(a)
6-[4-[Bis(2-hydroxyethyl)aminosulfonyl]phenyl]-1,2-dihydro-2-oxonicotinic Acid, 2,5-Dioxo-1-pyrrolidinyl Ester A solution of 45 g. of 6-[4-[bis(2-hydroxyethyl)aminosulfonyl]phenyl]-1,2-dihydro-2-oxonicotinic acid and 14.0 g. of N-hydroxysuccinimide in 450 ml. of dimethylformamide is cooled to 0°–5° C. and treated dropwise, with stirring, with a solution of 26.8 g. of N,N'-dicyclohexylcarbodiimide in 30 ml. of dimethylformamide. The mixture is stirred for 16 hours at room temperature, then cooled and filtered to remove by-product N,N'-dicyclohexylurea. The filtrate is diluted with 1.5 l. of 2-propanol and the resulting precipitate of 6-[4-[bis(2-hydroxyethyl)aminosulfonyl]phenyl]-1,2-dihydro-2-oxonicotinic acid, 2,5-dioxo-1-pyrrolidinyl ester is collected by filtration, washed with cold 2-propanol and dried; m.p. 213°–215.5° C.

(b)
6-[4-[(2-Hydroxyethyl)aminosulfonyl]phenyl]-1,2-dihydro-2-oxonicotinic Acid, 2,5-Dioxo-1-pyrrolidinyl Ester From 3.8 g. of 6-[4-[(2-hydroxyethyl)aminosulfonyl]phenyl]-1,2-dihydro-2-oxonicotinic acid and 1.34 g. of N-hydroxysuccinimide in 60 ml. of dimethylformamide, and 2.56 g. of N,N'-dicyclohexylcarbodiimide in 5 ml. of dimethylformamide, following the procedure of (a) above, there is obtained 6-[4-[(2-hydroxyethyl)aminosulfonyl]phenyl]-1,2-dihydro-2-oxonicotinic acid, 2,5-dioxo-1-pyrrolidinyl ester; m.p. 203.5°–205° C.

(c)
6-[4-(3-Hydroxymethyl-1-piperidinylsulfonyl)phenyl]-1,2-dihydro-2-oxonicotinic Acid, 2,5-Dioxo-1-pyrrolidinyl Ester From 5.0 g. of 6-[4-(3-hydroxymethyl-1-piperidinylsulfonyl)phenyl]-1,2-dihydro-2-oxonicotinic acid in 130 ml. of dimethylformamide, and 2.89 g. of N,N'-dicyclohexylcarbodiimide in 10 ml. of dimethylformamide, following the procedure of (a) above, there is obtained 6-[4-(3-hydroxymethyl-1-piperidinylsulfonyl)phenyl]-1,2-dihydro-2-oxonicotinic acid, 2,5-dioxo-1-pyrrolidinyl ester; m.p. 201°–204° C.

(d)
6-[4-[Bis(2-hydroxyethyl)aminosulfonyl]phenyl]-1,2-dihydro-1-methyl-2-oxonicotinic acid, 2,5-dioxo-1-pyrrolidinyl Ester A solution of 4.43 g. of 6-[4-[bis(2-hydroxyethyl)aminosulfonyl]phenyl]-1,2-dihydro-1-methyl-2-oxonicotinic acid and 1.34 g. of N-hydroxysuccinimide in 60 ml. dimethylformamide was cooled in ice and treated dropwise with a solution of 2.56 g. of N,N'-dicyclohexylcarbodiimide in 5 ml. dimethylformamide. The solution was allowed to warm to room temperature over 16 hours. The mixture was cooled and the N,N'-dicyclohexylurea filtered off. Addition of 180 ml. of isopropanol to the filtrate precipitated the 6-[4-[bis(2-hydroxyethyl)aminosulfonyl]phenyl]-1,2-dihydro-1-methyl-2-oxonicotinic acid, 2,5-dioxo-1-pyrrolidinyl ester, which was collected by filtration.

H.
6-[4-(Dimethylaminosulfonyl)phenyl]-1,2-dihydro-2-oxonicotinyl Imidazolide

A stirred suspension of 4.0 g. of 6-[4-(dimethylaminosulfonyl)phenyl]-1,2-dihydro-2-oxonicotinic acid in 32 ml. of N,N-dimethylacetamide is treated with 2.82 g. of 1,1-carbonyldiimidazole. The mixture is stirred at 60° C. for 1 hour, cooled and diluted with 100 ml. of ether. The precipitate of 6-[4-(dimethylaminosulfonyl)phenyl]-1,2-dihydro-oxonicotinyl imidazolide is collected by filtration, washed with ether and dried.

I.
D-N-[6-[4-(Dimethylaminosulfonyl)phenyl]-1,2-dihydro-2-oxonicotinyl]-2-phenylglycine A mixture of 16.6 g. of D-(−)-2-phenylglycine, 30 ml. of trimethylsilyl chloride and 35 ml. of triethylamine in 1.0 l. of dichloromethane is stirred for 1 hour at room temperature. The resulting solution of D-N-(trimethylsilyl)-2-phenylglycine, trimethylsilyl ester, is cooled to 0°–5° C. and there is added in portions, with stirring, 34 g. of 6-[4-dimethylaminosulfonyl)phenyl]-1,2-dihydro-2-oxonicotinyl chloride, followed by 13.9 ml. of triethylamine. The mixture is stirred at 0°–5° C. for 1 hour, then at room temperature for 2 hours. The mixture is poured into 1 l. of ice water and the pH adjusted to 8.1 with saturated aqueous sodium bicarbonate. The aqueous solution is extracted with ethyl acetate and the extract discarded. The aqueous solution is then acidified to pH 2.0 with dilute hydrochloric acid. The resulting precipitate of D-N-[6-[4-(dimethylaminosulfonyl)phenyl]-1,2-dihydro-2-oxonicotinyl]-2-phenylglycine is collected by filtration, washed well with water and dried.

We claim:
1. A compound of the formula

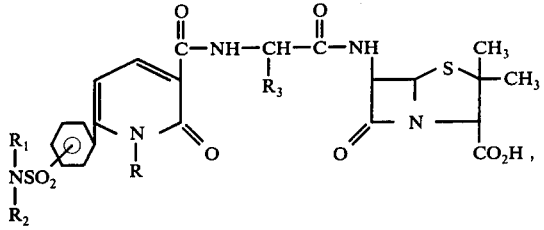

and pharmaceutically-acceptable salts thereof; wherein R is hydrogen or methyl; $R_1$ is hydrogen, lower alkyl or hydroxy(lower alkyl), $R_2$ is hydrogen, lower alkyl, hydroxy(lower alkyl), pyridyl or di(lower alkyl)amino(lower alkyl); $R_1R_2N$ taken together is 1-pyrrolidinyl, 1-piperidinyl or hydroxymethyl-1-piperidinyl, $R_3$ is phenyl, 4-hydroxyphenyl, 2-thienyl or cyclohexa-1,4-dien-1-yl.

2. The compounds of claim 1 wherein $R_1$ and $R_2$ are hydroxy(lower alkyl).

3. The compounds of claim 2 wherein the $R_1R_2NSO_2$ group is in the para position and $R_3$ is p-hydroxyphenyl.

4. The compound of claim 1 having the name N-[6-[4-[bis(2-hydroxyethyl)aminosulfonyl]phenyl]-1,2-dihydro-2-oxonicotinyl]ampicillin and pharmaceutically-acceptable salts thereof.

5. The compound of claim 1 having the name N-[6-[4-[bis(2-hydroxyethyl)aminosulfonyl]phenyl]-1,2-dihydro-2-oxonicotinyl]ampicillin, sodium salt.

6. The compound of claim 1 having the name N-[6-[4-[bis(2-hydroxyethyl)aminosulfonyl]phenyl]-1,2-dihydro-2-oxonicotinyl]amoxicillin and pharmaceutically-acceptable salts thereof.

7. The compound of claim 1 having the name N-[6-[4-[bis(2-hydroxyethyl)aminosulfonyl]phenyl]-1,2-dihydro-2-oxonicotinyl]amoxicillin, sodium salt.

8. The compound of claim 1 having the name N-[6-[4-(dimethylaminosulfonyl)phenyl]-1,2-dihydro-2-oxonicotinyl]amoxicillin and pharmaceutically-acceptable salts thereof.

9. The compound of claim 1 having the name N-[6-[4-(dimethylaminosulfonyl)phenyl]-1,2-dihydro-2-oxonicotinyl]amoxicillin, sodium salt.

10. The compound of claim 1 having the name N-[6-[4-[(2-dimethylaminoethyl)aminosulfonyl]phenyl]-1,2-dihydro-2-oxonicotinyl]amoxicillin and pharmaceutically-acceptable salts thereof.

11. The compound of claim 1 having the name N-[6-[4-[(2-dimethylaminoethyl)aminosulfonyl]phenyl]-1,2-dihydro-2-oxonicotinyl]amoxicillin, sodium salt.

12. An antibacterial composition consisting of an antibacterially effective amount of a compound of claim 1 and a pharmaceutical carrier.

13. A method for treating bacterial infections in mammals which comprises administering an antibacterially effective amount of composition of claim 12.

* * * * *